(12) United States Patent
Stack et al.

(10) Patent No.: US 7,470,799 B2
(45) Date of Patent: *Dec. 30, 2008

(54) DIHYDROBENZOFURAN DERIVATIVES AND USES THEREOF

(75) Inventors: Gary Paul Stack, Ambler, PA (US); Jonathan Laird Gross, Cranbury, NJ (US)

(73) Assignee: Wyeth, Madison, NJ (US)

( * ) Notice: Subject to any disclaimer, the term of this patent is extended or adjusted under 35 U.S.C. 154(b) by 75 days.

This patent is subject to a terminal disclaimer.

(21) Appl. No.: 11/408,653

(22) Filed: Apr. 21, 2006

(65) Prior Publication Data

US 2006/0246551 A1    Nov. 2, 2006

Related U.S. Application Data

(60) Provisional application No. 60/674,060, filed on Apr. 22, 2005.

(51) Int. Cl.
*C07D 307/00* (2006.01)
*A61K 31/34* (2006.01)

(52) U.S. Cl. ...................... 549/467; 514/469
(58) Field of Classification Search ............... 549/467; 514/469
See application file for complete search history.

(56) References Cited

U.S. PATENT DOCUMENTS

| | | | |
|---|---|---|---|
| 5,308,866 A | 5/1994 | Lesieur et al. |
| 5,541,228 A | 7/1996 | Takaki et al. |
| 6,211,225 B1 | 4/2001 | Takaki et al. |
| 6,214,869 B1 | 4/2001 | Chen et al. |
| 6,569,894 B1 | 5/2003 | Takaki et al. |
| 2003/0216456 A1 | 11/2003 | Takaki et al. |
| 2005/0124692 A1 | 6/2005 | Gross et al. |
| 2005/0143452 A1 | 6/2005 | Gross et al. |
| 2005/0261347 A1 | 11/2005 | Gross et al. |
| 2006/0089405 A1 | 4/2006 | Zhou |
| 2006/0111438 A1 | 5/2006 | Gontcharov et al. |
| 2006/0241172 A1 | 10/2006 | Zhou et al. |
| 2006/0241176 A1 | 10/2006 | Stack et al. |
| 2006/0246551 A1 | 11/2006 | Stack et al. |
| 2006/0247276 A1 | 11/2006 | Gross et al. |
| 2006/0252825 A1 | 11/2006 | Tadayon et al. |
| 2006/0258639 A1 | 11/2006 | Logue et al. |
| 2006/0258711 A1 | 11/2006 | Rosenzweig-Lipson |
| 2006/0258712 A1 | 11/2006 | Jacobson |
| 2006/0258713 A1 | 11/2006 | Rosenzweig-Lipson |
| 2006/0258714 A1 | 11/2006 | Heffernan et al. |
| 2006/0258715 A1 | 11/2006 | Jandura et al. |
| 2006/0258739 A1 | 11/2006 | Ai et al. |

FOREIGN PATENT DOCUMENTS

| | | |
|---|---|---|
| EP | 0718286 (A) | 6/1996 |
| WO | WO 97/06140 (A) | 2/1997 |
| WO | WO 2006/000902 | 5/2006 |

OTHER PUBLICATIONS

U.S. Appl. No. 11/787,929, Yu et al.
U.S. Appl. No. 11/787,860, Gontcharov et al.
U.S. Appl. No. 11/726,941, Rosenzweig-Lipson.
U.S. Appl. No. 11/787,663, Mirmehrabi.
Papp, M., et al., Neuropsychopharmacology, 28(4), 694 (2003).
Bourin, M., et al., Journal of Psychiatry and Neuroscience, 29(2), 126 (2004).
Loo, H., et al., L'Encephale, 29(2), 165 (2003).
Bundgaard, et al., Journal of Drug Delivery Reviews, 8: 1-38 (1992).
Millan, M. J., et al., Neuropharmacology 37: 953-955, 1998.
Di Matteo, V., et al., Neuropharmacology, 38: 1195-1205, 1999.
Di Giovanni, G., et al., Synapse, 35: 53-61, 2000.
Bundgaard, J. of Pharmaceutical Sciences, 77: 285 et seq. (1988).
Cowen, P. J., et al., Human Psychopharmacology 10: 385-391, 1995.
Rosenzweig-Lipson, S., et al., ASPET abstract, 2000.
Wilen, S. H., et al., Tetrahedron, 33: 2725 (1977).
Audinot, V., et al., "New selective ligands of human cloned melatonin MT1 and MT2 receptors," Nauyn-Schmiedeberg's Arch Pharmacol, 2003, 367: 553-561.
International Search Report for PCT/US2006/015172, mailed Oct. 5, 2006.
Written Opinion of International Searching Authority, PCT/US2006/015172, mailed Oct. 5, 2006.

*Primary Examiner*—D. Margaret Seaman
*Assistant Examiner*—Nizal S Chandrakumar
(74) *Attorney, Agent, or Firm*—Andrea L. Robidoux; Julie Anne Knight; Choate Hall & Stewart LLP

(57) ABSTRACT

Compounds of formula I are provided:

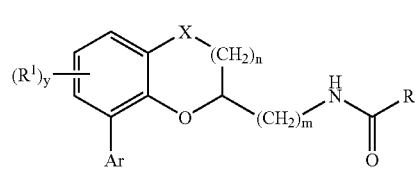

wherein each of $R^1$, $R^2$, y, m, n, and Ar are as defined, and described in classes and subclasses herein, which are agonists or partial agonists of melatoninergic receptors. The compounds, and compositions containing the compounds, can be used to treat melatoninergic disorders.

13 Claims, No Drawings

DIHYDROBENZOFURAN DERIVATIVES AND USES THEREOF

CROSS REFERENCE TO RELATED APPLICATIONS

This application claims priority to U.S. Provisional Patent Application Ser. No. 60/674,060, filed Apr. 22, 2005, the entirety of which is hereby incorporated herein by reference.

FIELD OF THE INVENTION

The present invention relates to melatonin agonists or partial agonists, processes for their preparation, and uses thereof.

BACKGROUND OF THE INVENTION

Melatonin, which is a widely used over-the-counter therapy for the treatment of sleep disorders, is a natural hormone produced and secreted by the pineal gland. It acts at two G-protein coupled receptors (MT1 and MT2), which are negatively coupled to adenylyl cyclase and which play a role in the regulation of sleep and circadian rhythym by controlling neuronal firing in the suprachiasmatic nucleus of the thalamus. Melatonin agonists and partial agonists have the potential to improve sleep quality by resynchronizing the disrupted rhythymicity of sleep/wake cycles.

In addition, melatonin agonists such as agomelatine have been shown to be active in animal models predictive of clinical antidepressant efficacy, such as the Chronic Mild Stress model [Neuropsychopharmacology 28(4), 694 (2003)] and the Forced Swim Test [Journal of Psychiatry and Neuroscience, 29(2), 126 (2004)]. Agomelatine has recently been reported to be active in clinical trials for the treatment of depression [L'Encephale 29(2), 165 (2003) and www.medicalnewstoday.com, Apr. 5, 2005].

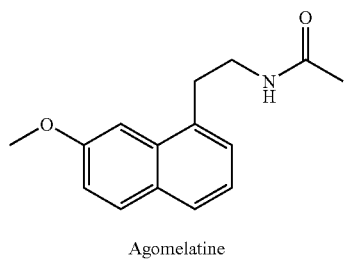

Agomelatine

The compounds of the present invention have potent affinity for melatonin MT1 and MT2 receptors and are thus useful for controlling sleep disorders and for the treatment of depression. In addition, the compounds of the present invention are capable of being hydrolyzed in vivo (ie, acting as pro-drugs) to agents with potent agonist and partial agonist effects at serotonin $5\text{-HT}_{2C}$ receptors. $5\text{-HT}_{2C}$ agonists represent a novel therapeutic approach toward the treatment of schizophrenia. Several lines of evidence support a role for $5\text{-HT}_{2C}$ receptor agonism as a treatment for schizophrenia. Recent studies have demonstrated that $5\text{-HT}_{2C}$ agonists decrease levels of dopamine in the prefrontal cortex and nucleus accumbens (Millan, M. J., et. al., Neuropharmacology 37: 953-955, 1998; Di Matteo, V., et. al., Neuropharmacology 38: 1195-1205, 1999; Di Giovanni, G., et. al., Synapse 35: 53-61, 2000), brain regions that are thought to mediate critical antipsychotic effects of drugs like clozapine. In contrast, $5\text{-HT}_{2C}$ agonists do not decrease dopamine levels in the striatum, the brain region most closely associated with extrapyramidal side effects. In addition, a recent study demonstrates that $5\text{-HT}_{2C}$ agonists decrease firing in the ventral tegmental area (VTA), but not in substantia nigra Di Matteo and Di Giovanni, op. cit.). The differential effects of $5\text{-HT}_{2C}$ agonists in the mesolimbic pathway relative to the nigrostriatal pathway suggests that $5\text{-HT}_{2C}$ agonists will have limbic selectivity and will be less likely to produce extrapyramidal side effects associated with typical antipsychotics.

Atypical antipsychotics bind with high affinity to $5\text{-HT}_{2C}$ receptors and function as $5\text{-HT}_{2C}$ receptor antagonists or inverse agonists. Weight gain is a problematic side effect associated with atypical antipsychotics such as clozapine and olanzapine and it has been suggested that $5\text{-HT}_{2C}$ antagonism is responsible for the increased weight gain. Conversely, stimulation of the $5\text{-HT}_{2C}$ receptor is known to result in decreased food intake and body weight (Walsh et. al., Psychopharmacology 124: 57-73, 1996; Cowen, P. J., et. al., Human Psychopharmacology 10: 385-391, 1995; Rosenzweig-Lipson, S., et. al., ASPET abstract, 2000). As a result, $5\text{-HT}_{2C}$ agonists will be less likely to produce the body weight increases associated with current atypical antipsychotics. Indeed, $5\text{-HT}_{2C}$ agonists are of great interest for the treatment of obesity, a medical disorder characterized by an excess of body fat or adipose tissue and associated with such comorbidities as Type II diabetes, cardiovascular disease, hypertension, hyperlipidemia, stroke, osteoarthritis, sleep apnea, gall bladder disease, gout, some cancers, some infertility, and early mortality. Other therapeutic indications for $5\text{-HT}_{2C}$ agonists are obsessive compulsive disorder, depression, panic disorder, sleep disorders, eating disorders and epilepsy.

SUMMARY OF THE INVENTION

The present invention relates to certain melatonin agonists or partial agonists and uses thereof. The compounds of the present invention are useful, for example, to treat depression and sleep disorders.

In certain embodiments, the invention provides a compound of formula I:

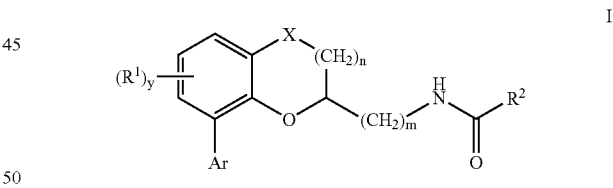

I or pharmaceutically acceptable salts thereof, wherein:
m is 1 or 2;
n is 0 or 1;
y is 0, 1, 2, or 3;
each $R^1$ is independently —CN, halogen, —R, or —OR;
each R is independently hydrogen, $C_{1-4}$ aliphatic, or fluoro-substituted $C_{1-4}$ aliphatic;
Ar is thienyl, furyl, pyridyl, or phenyl wherein Ar is optionally substituted with one or more $R^x$ groups;
each $R^x$ is independently halogen, phenyl, —CN, —R, or —OR;
$R^2$ is hydrogen or $C_{1-4}$ aliphatic; and
X is —O—, —S—, —S(O)—, —SO$_2$— or —CH$_2$—.

In certain other embodiments, the invention relates to methods for treating a patient suffering from a melatoninergic disorder comprising administering to the patient a therapeutically effective amount of a compound of formula I, or a pharmaceutically acceptable salt thereof.

In still other embodiments, the invention relates to compositions comprising a compound of formula I or a pharmaceutically acceptable salt thereof, and one or more pharmaceutically acceptable carriers, excipients, or diluents.

DETAILED DESCRIPTION OF THE INVENTION

1. Compounds and Definitions:

The present invention relates to compounds as described herein that are agonists or partial agonists of melatonin.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. In certain embodiments, aliphatic groups contain 1-4 aliphatic carbon atoms, and in yet other embodiments, aliphatic groups contain 1-3 aliphatic carbon atoms. In some embodiments, "cycloaliphatic" (or "carbocycle" or "cycloalkyl") refers to a monocyclic $C_3$-$C_4$ hydrocarbon that is completely saturated or that contains one or more units of unsaturation and has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "unsaturated," as used herein, means that a moiety has one or more units of unsaturation.

The term "fluoro-substituted," as used herein, means that one or more hydrogen atoms are replaced by fluorine atoms. In certain embodiments, the term fluoro-substituted aliphatic refers to perfluoro-substituted aliphatic in which all hydrogen atoms are replaced by fluorine atoms. Such groups include —$CF_3$.

The term "lower alkyl," as used herein, refers to a hydrocarbon chain having up to 4 carbon atoms, preferably 1 to 3 carbon atoms, and more preferably 1 to 2 carbon atoms. The term "alkyl" includes, but is not limited to, straight and branched chains such as methyl, ethyl, n-propyl, isopropyl, n-butyl, isobutyl, sec-butyl, or t-butyl.

The term "alkoxy," as used herein, refers to the group —OR*, wherein R* is a lower alkyl group.

The terms "halogen" or "halo," as used herein, refer to chlorine, bromine, fluorine or iodine.

The term "alkenyl," as used herein refers to an aliphatic straight or branched hydrocarbon chain having 2 to 4 carbon atoms that may contain 1 to 3 double bonds. Examples of alkenyl groups include vinyl, prop-1-enyl, allyl, methallyl, but-1-enyl, but-2-enyl, but-3-enyl, or 3,3-dimethylbut-1-enyl. In some embodiments, the alkenyl is preferably a branched alkenyl of 3 to 4 carbon atoms. The term "lower alkenyl" refers to an alkenyl group having 1 to 3 carbon atoms.

The terms "effective amount" and "therapeutically effective amount," as used herein, refer to the amount of a compound of formula I that, when administered to a patient, is effective to at least partially treat a condition from which the patient is suffering. Such conditions include, melatoninergic disorders including, but not limited to, depression and sleep disorders.

The term "pharmaceutically acceptable salts" or "pharmaceutically acceptable salt" refers to salts derived from treating a compound of formula I with an organic or inorganic acid such as, for example, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, or similarly known acceptable acids. In certain embodiments, the present invention relates to the hydrochloride salt of a compound of formula I.

The term "patient," as used herein, refers to a mammal. In certain embodiments, the term "patient," as used herein, refers to a human.

The terms "administer," "administering," or "administration," as used herein, refer to either directly administering a compound or composition to a patient, or administering a prodrug derivative or analog of the compound to the patient, which will form an equivalent amount of the active compound or substance within the patient's body.

The terms "treat" or "treating," as used herein, refers to partially or completely alleviating, inhibiting, preventing, ameliorating and/or relieving the condition.

The terms "suffer" or "suffering," as used herein, refers to one or more conditions that a patient has been diagnosed with, or is suspected to have.

2. Description of Exemplary Compounds:

In certain embodiments, the invention relates to a compound of formula I:

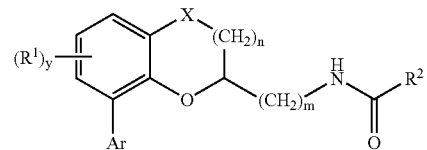

I or pharmaceutically acceptable salts thereof, wherein:

m is 1 or 2;

n is 0 or 1;

y is 0, 1, 2, or 3;

each $R^1$ is independently —CN, halogen, —R, or —OR;

each R is independently hydrogen, $C_{1-4}$ aliphatic, or fluoro-substituted $C_{1-4}$ aliphatic;

Ar is thienyl, furyl, pyridyl, or phenyl wherein Ar is optionally substituted with one or more $R^x$ groups;

each $R^x$ is independently halogen, phenyl, —CN, —R, or —OR;

$R^2$ is hydrogen or $C_{1-4}$ aliphatic; and

X is O, S, S(O), $SO_2$ or $CH_2$.

As defined generally above, the n group of formula I is 0 or 1. In certain embodiments, n is 1 thus forming a compound of formula Ia:

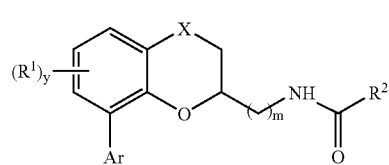

Ia or a pharmaceutically acceptable salt thereof, wherein $R^1$, $R^2$, X, Ar, y, and m are as defined above for compounds of formula I and in classes and subclasses as described above and herein.

According to another embodiment, the n group of formula I is 0, thus forming a compound of formula Ib:

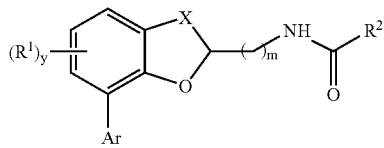

or a pharmaceutically acceptable salt thereof, wherein $R^1$, $R^2$, X, Ar, y, and m are as defined above for compounds of formula I and in classes and subclasses as described above and herein.

As defined generally above, y is 0-3 and each $R^1$ group of formula I is independently —CN, halogen, —R, or —OR. In certain embodiments, y is 0. In other embodiments, y is other than 0 and at least one $R^1$ group of formula I is halogen. In still other embodiments, y is 1, and $R^1$ is halogen, methyl, or ethyl.

According to one embodiment, y is 1, n is 1, and $R^1$ is at the 6- or 7-position of the bicyclic ring of formula I, thus forming a compound of formula IIa or IIb:

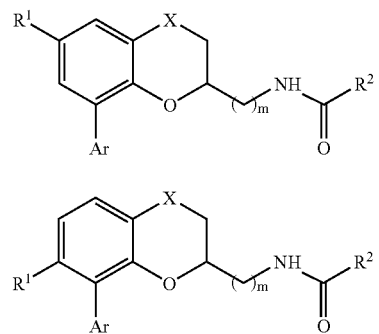

or a pharmaceutically acceptable salt thereof, wherein each $R^1$, $R^2$, X, Ar, and m are as defined above for compounds of formula I and in classes and subclasses as described above and herein.

According to another embodiment, y is 1, n is 0, and $R^1$ is at the 5- or 6-position of the bicyclic ring of formula I, thus forming a compound of formula IIc or IId:

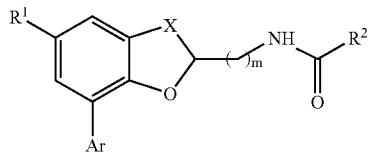

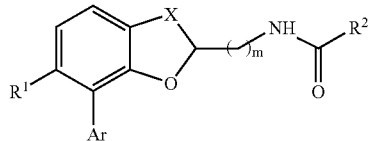

or a pharmaceutically acceptable salt thereof, wherein each $R^1$, $R^2$, X, Ar, and m are as defined above for compounds of formula I and in classes and subclasses as described above and herein.

As defined generally above, the Ar group of formula I is thienyl, furyl, pyridyl, or phenyl, wherein Ar is optionally substituted with one or more subsituents independently selected from halogen, phenyl, —CN, —R, or —OR. In certain embodiments, the Ar group of formula I is unsubstituted phenyl. In other embodiments, the Ar group of formula I is phenyl with at least one substituent in the ortho position. In other embodiments, the Ar group of formula I is phenyl with at least one substituent in the ortho position selected from halogen, lower alkyl, lower alkoxy, or trifluoromethyl. According to another aspect the present invention provides a compound of formula I wherein Ar is phenyl disubstituted in the ortho and meta positions with independently selected halogen, lower alkyl, or lower alkoxy. Yet another aspect of the present invention provides a compound of formula I wherein Ar is phenyl disubsituted in the ortho and para positions with independently selected halogen lower alkyl, or lower alkoxy. In other embodiments, the present invention provides a compound of formula I wherein Ar is phenyl disubstituted in the ortho positions with independently selected halogen, lower alkyl, or lower alkoxy. Exemplary substituents on the phenyl moiety of the Ar group of formula I include OMe, fluoro, chloro, methyl, and trifluoromethyl.

In certain embodiments, the present invention provides a compound of formula IId wherein Ar is phenyl with one substituent in the ortho position selected from halogen, lower alkyl, lower alkoxy, or trifluoromethyl.

According to one embodiment, Ar is phenyl substituted with $R^x$ in the ortho-position thus forming a compound of formula IIIa or IIIb:

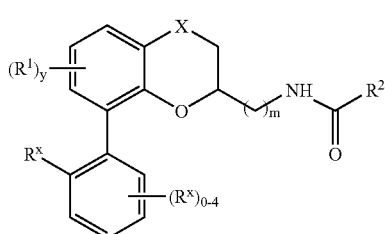

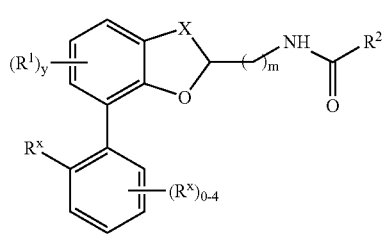

wherein each R¹, R², X, Rˣ, y and m are as defined above for compounds of formula I and in classes and subclasses as described above and herein.

In certain embodiments, Ar is phenyl disubstituted with Rˣ in the ortho-positions thus forming a compound of formula IVa or IVb:

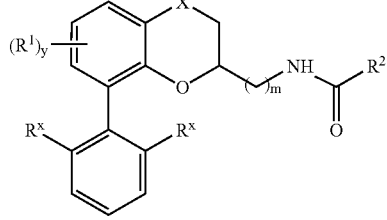

IVa

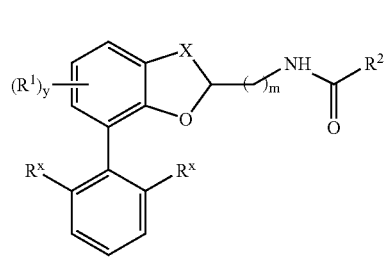

IVb wherein each R¹, R², X, Rˣ, y and m are as defined above for compounds of formula I and in classes and subclasses as described above and herein.

According to another embodiment, the present invention provides a compound of formula IVc or IVd:

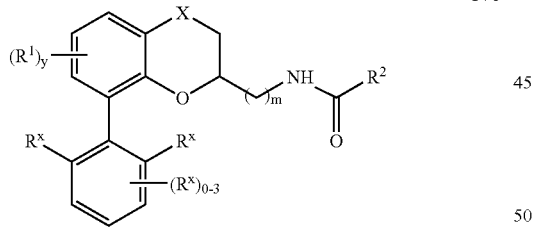

IVc

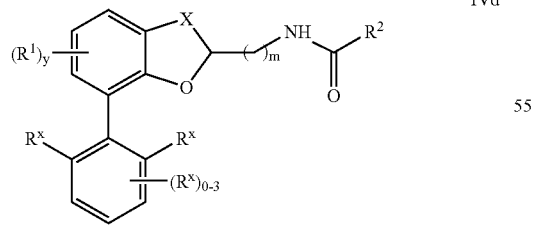

IVd wherein each R¹, R², X, Rˣ, y and m are as defined above for compounds of formula I and in classes and subclasses as described above and herein.

In certain embodiments, the Ar group of formula I is selected from the following:

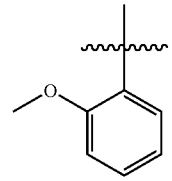

i

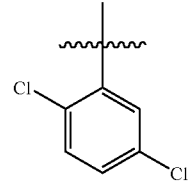

ii

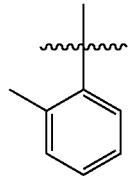

iii

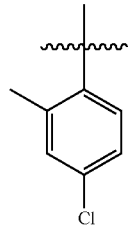

iv

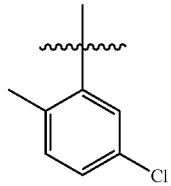

v

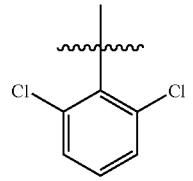

vi

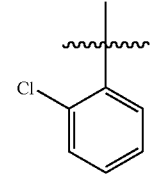

vii viii

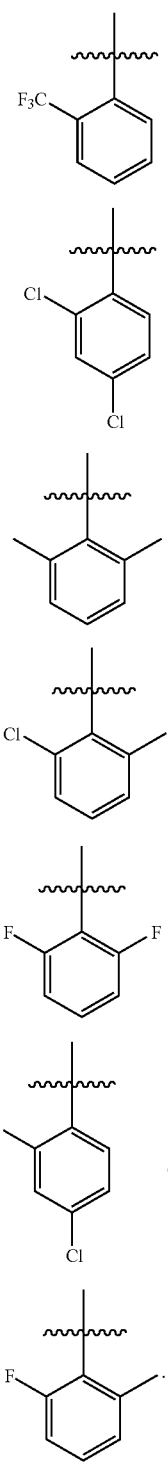

As defined generally above, the $R^2$ of formula I is hydrogen or $C_{1-4}$ aliphatic. In certain embodiments, the $R^2$ of formula I is hydrogen, methyl, ethyl, propyl, cyclopropyl or cyclobutyl. In other embodiments, the $R^2$ group of formula I is hydrogen, methyl or ethyl. In yet other embodiments, $R^2$ is methyl.

According to another embodiment, the present invention provides a compound of formula I wherein X is O or $CH_2$, m is 1 or 2, and n is 0 or 1. According to yet another embodiment, X is $CH_2$, m is 1, and n is 0, thus forming a compound of formula IV:

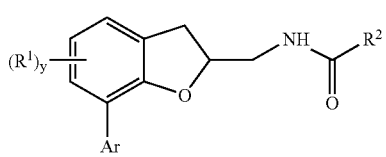

IV wherein each $R^1$, $R^2$, and Ar are as defined above for compounds of formula I and in classes and subclasses as described above and herein.

Compounds of the present invention contain asymmetric carbon atoms and thus give rise to stereoisomers, including enantiomers and diastereomers. Accordingly, it is contemplated that the present invention relates to all of these stereoisomers, as well as to mixtures of the stereoisomers. Throughout this application, the name of the product of this invention, where the absolute configuration of an asymmetric center is not indicated, is intended to embrace the individual stereoisomers as well as mixtures of stereoisomers. In certain embodiments of the invention, compounds having an absolute (R) configuration are preferred.

In certain embodiments, the present invention provides a compound of formula Va, Vb, Vc, or Vd:

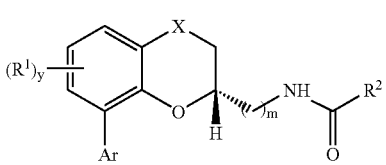

Va

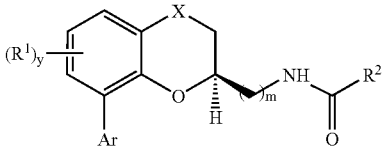

Vb

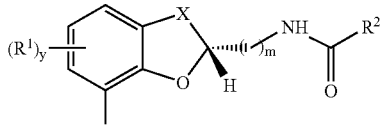

Vc

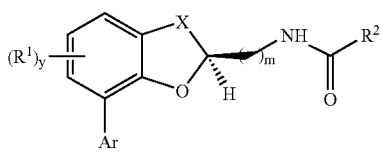

Vd wherein each $R^1$, $R^2$, X, Ar, y and m are as defined above for compounds of formula I and in classes and subclasses as described above and herein.

According to another embodiment, the present invention provides a compound of formula VIa, VIb, VIc, or VId:

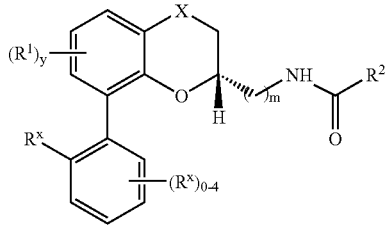
VIa

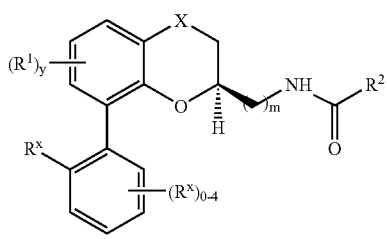
VIb

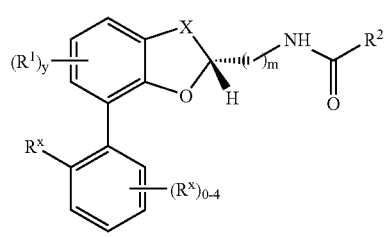
VIc

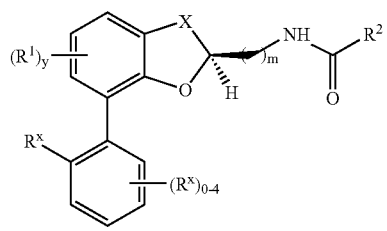
VId wherein each $R^1$, $R^2$, X, $R^x$, y and m are as defined above for compounds of formula I and in classes and subclasses as described above and herein.

According to another aspect of the present invention, a compound of formula VIIa or VIIb is provided:

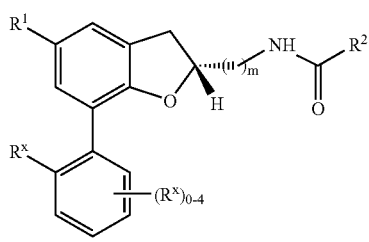
VIIa

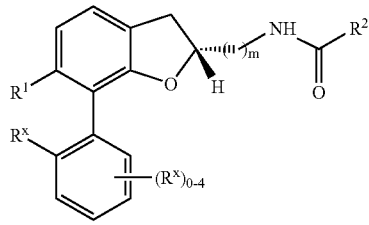
VIIb wherein each $R^1$, $R^2$, X, $R^x$, and m are as defined above for compounds of formula I and in classes and subclasses as described above and herein.

Where an enantiomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. "Substantially free," as used herein, means that the compound is made up of a significantly greater proportion of one enantiomer. In certain embodiments the compound is made up of at least about 90% by weight of a preferred enantiomer. In other embodiments of the invention, the compound is made up of at least about 99% by weight of a preferred enantiomer. Preferred enantiomers may be isolated from racemic mixtures by any method known to those skilled in the art, including chiral high pressure liquid chromatography (HPLC) and the formation and crystallization of chiral salts of intermediates of the compounds as described herein or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N.Y., 1962); Wilen, S. H. *Tables of Resolving Agents and Optical Resolutions* p. 268 (E. L. Eliel, Ed., Univ. of Notre Dame Press, Notre Dame, Ind. 1972).

It is further recognized that atropisomers of the present compounds may exit. The present invention thus encompasses atropisomeric forms of compounds of formula I as defined above, and in classes and subclasses described above and herein.

Exemplary compounds of formula I are set forth in Table 1, below.

TABLE 1

Exemplary Compounds of Formula I:

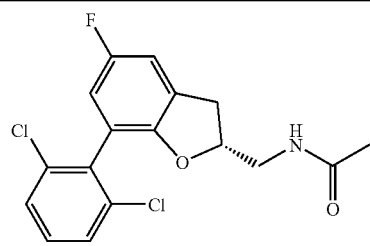

I-1

TABLE 1-continued
Exemplary Compounds of Formula I:
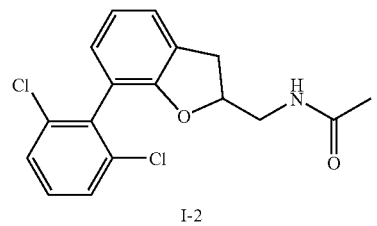
I-2
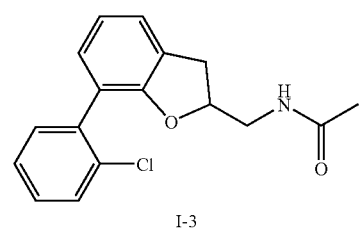
I-3
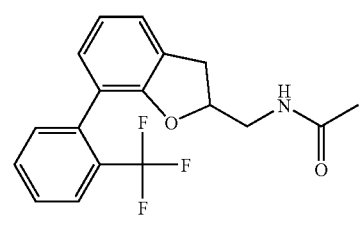
I-4
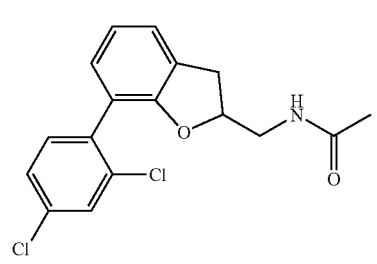
I-5
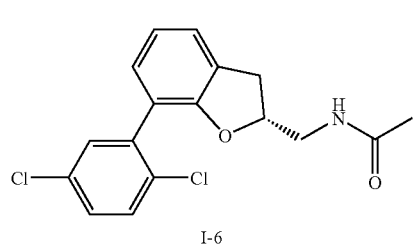
I-6
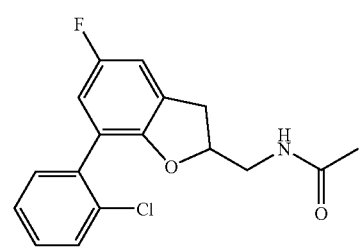
I-7
TABLE 1-continued
Exemplary Compounds of Formula I:
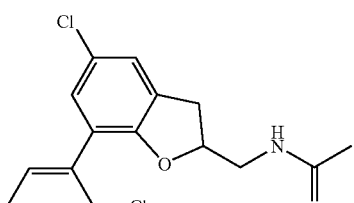
I-8
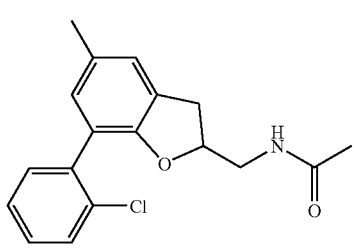
I-9
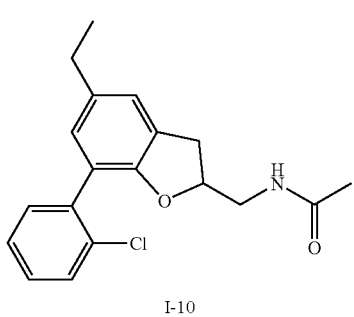
I-10
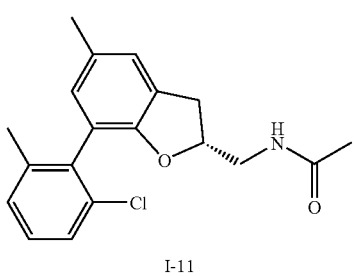
I-11
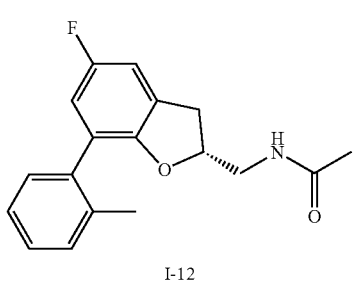
I-12

TABLE 1-continued

Exemplary Compounds of Formula I:

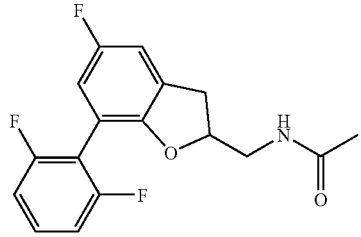
I-13

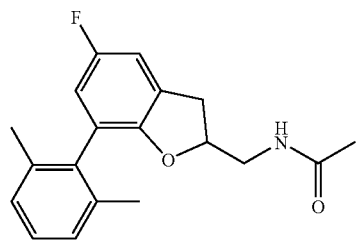
I-14

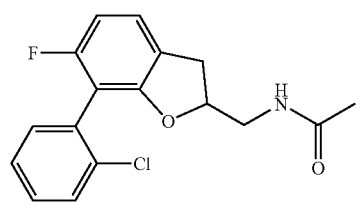
I-15

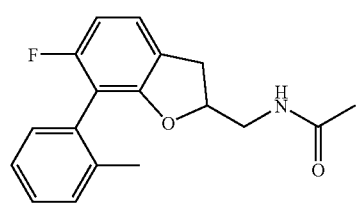
I-16

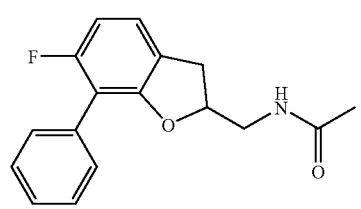
I-17

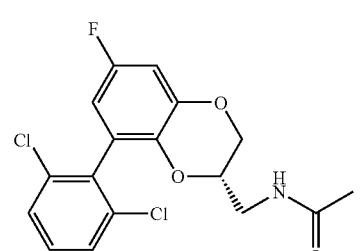
I-18

TABLE 1-continued

Exemplary Compounds of Formula I:

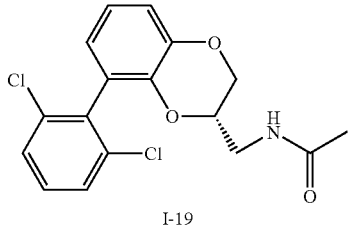
I-19

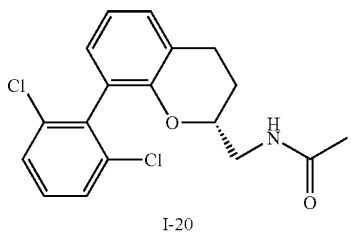
I-20

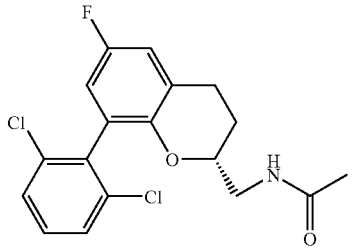
I-21

3. General Methods of Providing the Present Compounds:

The dihydrobenzofuran derivatives of the present invention are prepared as illustrated in Scheme 1, below. Unless otherwise noted, the variables are as defined above. Specifically, the appropriately substituted o-bromoanisole is converted to the corresponding boronic acid via metallation with n-butyl lithium, treatment of the lithio derivative with triisopropyl borate and hydrolysis of the resulting borate ester with aqueous hydrochloric acid. The boronic acid thus obtained was then caused to undergo a Suzuki coupling reaction by treatment with the appropriately substituted aryl bromide in the presence of a suitable palladium catalyst such as tetrakis(triphenylphosphine)palladium(0) and a base such as sodium carbonate. The ether is then cleaved via treatment with a demethylating agent such as boron tribromide and the resulting phenol alkylated with allyl bromide in the presence of a base such as sodium carbonate. The bi-aryl allyl ether is caused to undergo a Claisen rearrangement via refluxing in a high boiling solvent such as decahydronaphthalene, mesitylene or dimethylaniline and the rearranged olefin is then epoxidized with m-chloroperoxybenzoic acid. Treatment with a base such as sodium carbonate in methanol catalyzes the ring closure to the dihydrobenzofuran methanol. The resulting alcohol is converted to a leaving group via treatment with p-toluenesulfonyl chloride in pyridine and the tosylate displaced with sodium azide in a suitable solvent such as N,N-dimethylformamide. Reduction of the azide by hydrogenation over a suitable catalyst such as sulfided platinum on carbon and acylation of the resulting primary amine with a suitable acid chloride or anhydride in the presence of a base such as diisopropylethylamine gives the dihydrobenzofuran title compounds of the invention (I).

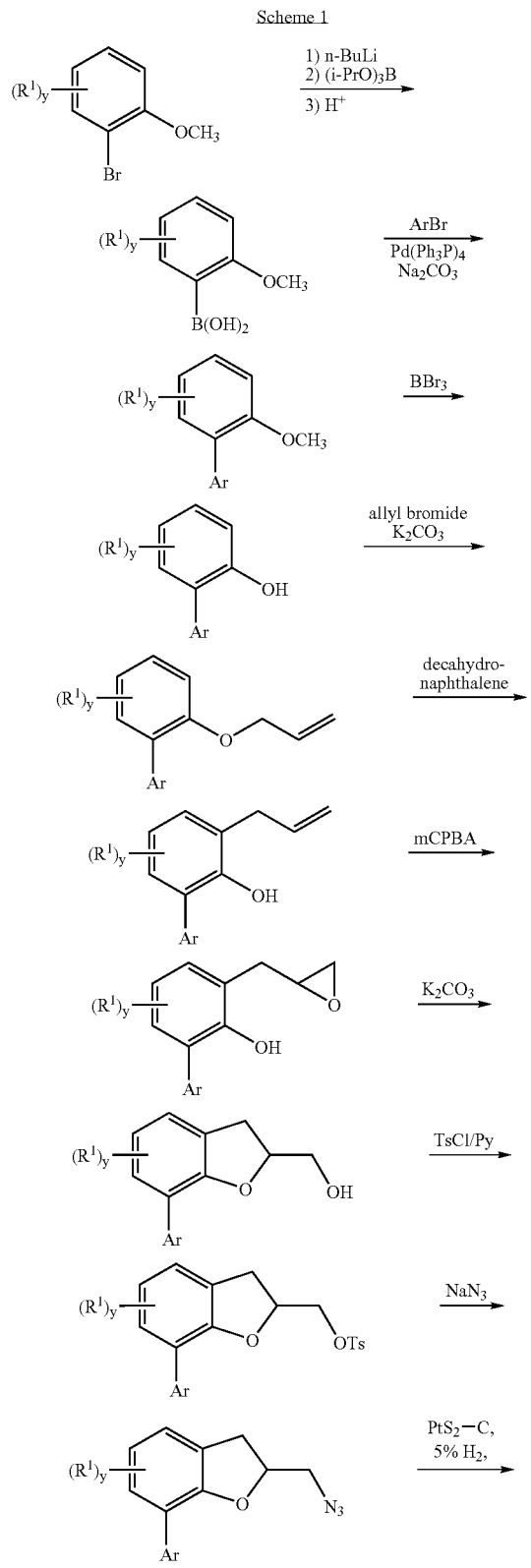

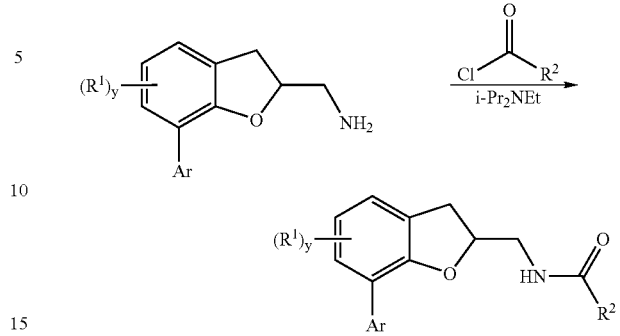

Alternatively, as shown in Scheme 2 below, the appropriately substituted o-bromophenol is alkylated with allyl bromide in the presence of a suitable base such as sodium carbonate and the resulting ether caused to undergo the Claisen rearrangement via reflux in a high boiling solvent such as decahydronaphthalene, mesitylene or N,N-dimethylaniline. The rearranged olefin is then epoxidized by treatment with m-chloroperoxbenzoic acid and the resulting epoxide cyclized to the dihydrobenzofuran methanol by treatment with a base such as sodium carbonate in methanol. The primary alcohol is then converted to the p-toluenesulfonylate by treatment with p-toluenesulfonyl chloride in pyridine. The resulting bromo-substituted dihydrobenzofuran methyltosylate is then made to undergo Suzuki coupling reactions by treatment with the appropriately substituted aryl boronic acids in the presence of a suitable palladium catalyst such as tetrakis(triphenylphosphine)palladium(0) and a base such as sodium carbonate. As before, replacement of the tosylate with azide, followed by azide reduction and acylation with the appropriate acyl chloride or anhydride gives the title compounds (I) of the invention.

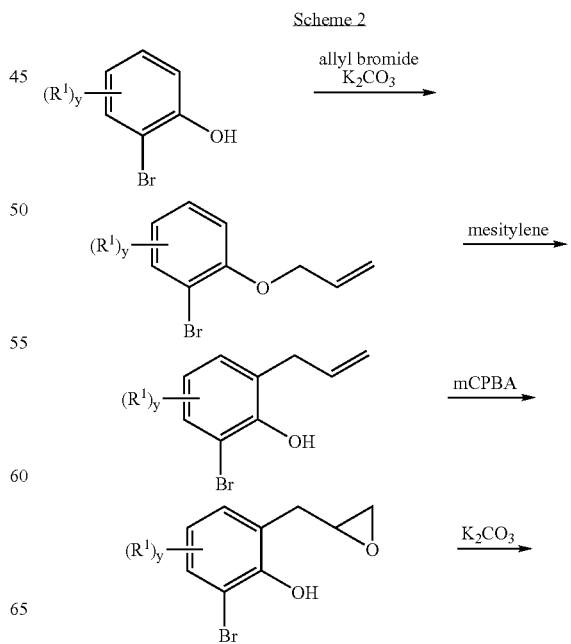

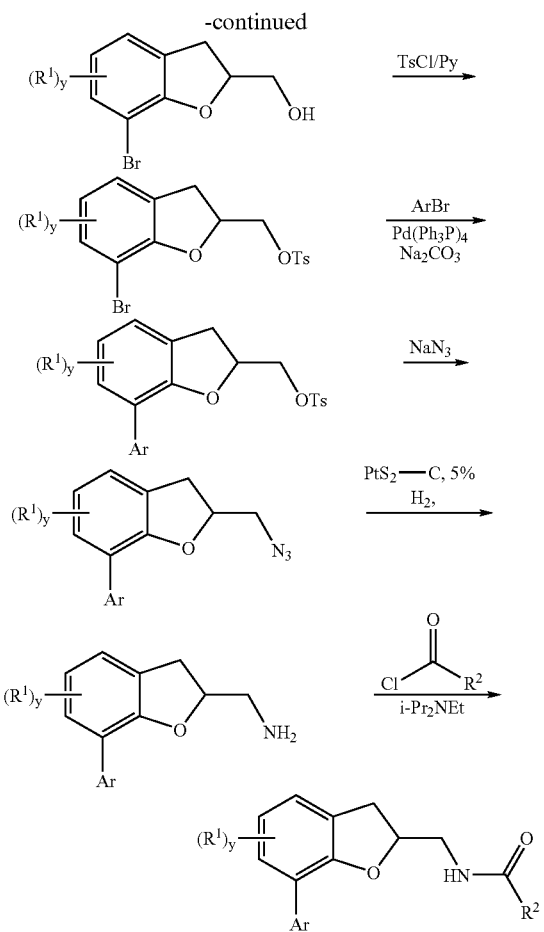

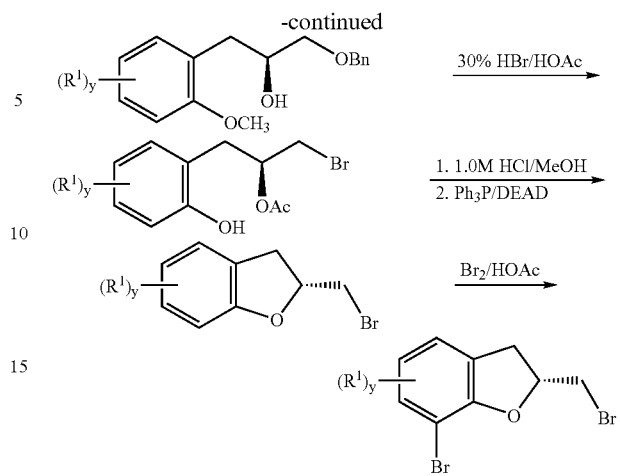

The compounds of the invention may also be prepared in a stereospecific manner via Scheme 3 below. The appropriately substituted o-bromo anisole is metallated by treatment with n-butyl lithium and converted to the cuprate via reaction with copper (I) bromide dimethyl sulfide complex. The resulting cuprate is caused to react with the epoxide moiety of enantiopure (R)- or (S)-glycidyl benzyl ether in the presence of a catalyst such as boron trifluoride etherate. The resulting protected glycol is demethylated and converted to the bromoacetate by treatment with 30% hydrogen bromide in acetic acid. Following hydrolysis of the acetyl group with hydrogen chloride in methanol, the dihydrobenzofuran ring is formed via a Mitsonobu reaction by treatment with triphenylphosphine and diethylazidodicarboxylate. The resulting dihydrobenzofuran methylbromide is then brominated by treatment with bromine in acetic acid. Following the same sequences shown in Scheme 2, the title compounds (I) of the invention can be made.

According to an alternate method, as depicted in Scheme 4 below, the appropriately substituted o-methoxyphenylboronic acid is caused to undergo the Suzuki coupling by treatment with the appropriately substituted aryl bromide in the presence of a suitable palladium catalyst such as tetrakis(triphenylphosphine)palladium(0) and a base such as sodium hydroxide. The resulting bi-aryl methyl ether is brominated with N-bromosuccinamide in acetic acid. The bromo compound is then converted to the Grignard reagent via exchange with isopropyl magnesium chloride and then to the cuprate by treatment with copper(I)iodide. The resulting cuprate is caused to react with the epoxide moiety of enantiopure (R)- or (S)-glycidyl p-tosylate to give the glycol mono-p-tosylate. Reaction with potassium phthalimide is followed by conversion of the secondary alcohol to the mesylate by reaction with methanesulfonyl chloride and triethylamine. Demethylation under the influence of boron tribromide and ring closure by treatment with a suitable base such as sodium carbonate gives the enantiopure dihydrobenzofuran. Removal of the phthalimido protecting group with hydrazine and acylation of the resulting amine with the appropriate acyl chlorides or anhydrides gives the compounds of the invention.

Scheme 3

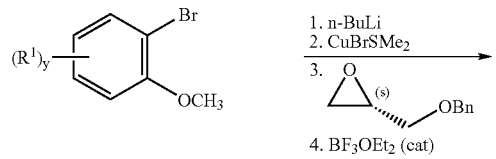

Scheme 4

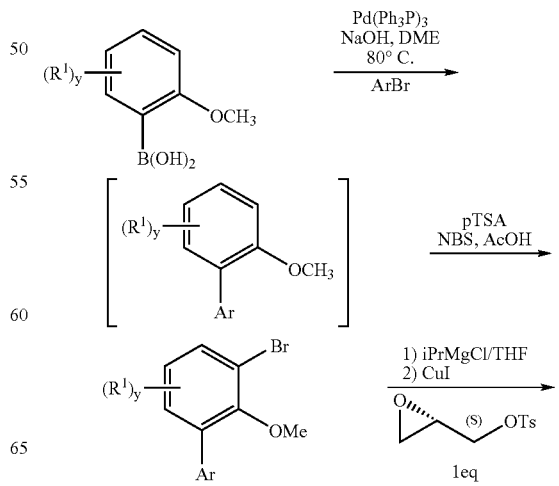

-continued

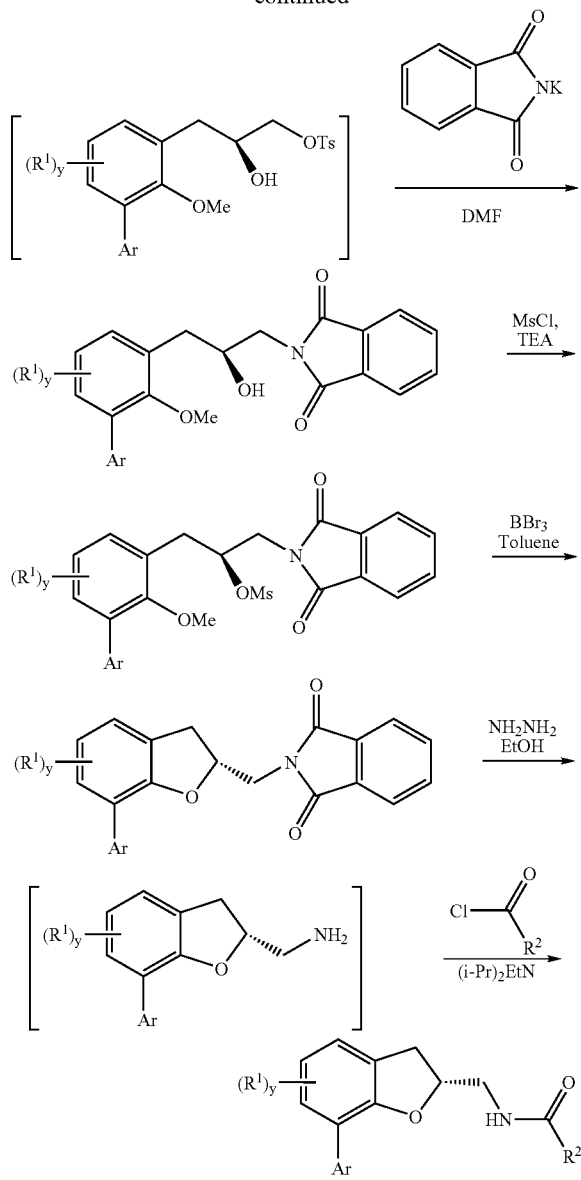

In addition to the synthetic methods described above, the stereoisomers of the present invention are also prepared by the stereoselective processes described in U.S. provisional patent application Ser. No. 60/621,023, filed Oct. 21, 2004, and U.S. provisional patent application Ser. No. 60/621,024, filed Oct. 21, 2004, the entirety of both of which is hereby incorporated herein by reference.

Although certain exemplary embodiments are depicted and described above and herein, it will be appreciated that compounds of the invention can be prepared according to the methods described generally above using appropriate starting materials by methods generally available to one of ordinary skill in the art. Additional embodiments are exemplified in more detail herein.

4. Uses, Formulation and Administration

Compounds of the present invention have affinity for and agonist or partial agonist activity for melatonin receptors and are thus of interest for the treatment of melatoninergic related disorders. As used herein, the term "melatoninergic disorder" means any disease or other deleterious condition in which a deficiency in melatonin is known to play a role. The term "melatoninergic disorder" also means those diseases or conditions that are alleviated by treatment with a melatoninergic agonist or partial agonist. In certain embodiments, such melatoninergic disorders include circadian rhythm disorders, depression, sleep disorders, Parkinson's disease, Alzheimer's disease, obesity, and diabetes. A more complete description of the aforementioned mental disorders can be found in the Diagnostic and Statistical Manual of Mental Disorders, 4$^{th}$ edition, Washington, D.C., American Psychiatric Association (1994), incorporated herein by reference in its entirety.

In certain embodiments, the compounds of the present invention are useful for treating stress, sleep disorders, anxiety, seasonal affective disorder, cardiovascular pathologies, pathologies of the digestive system, insomnia and fatigue due to jetlag, schizophrenia, panic attacks, melancholia, appetite disorders, obesity, insomnia, psychotic disorders, epilepsy, diabetes, Parkinson's disease, senile dementia, various disorders associated with normal or pathological ageing, migraine, memory loss, Alzheimer's disease, or in cerebral circulation disorders. In another embodiment, compounds of the present invention are useful for the treatment of sexual dysfunctions, and have ovulation-inhibiting and immunomodulating properties.

In other embodiments, the compounds of the present invention are useful for treating seasonal affective disorder, sleep disorders, cardiovascular pathologies, insomnia and fatigue due to jetlag, appetite disorders or obesity.

In still other embodiments, the compounds of the present invention are useful for treating depression or sleep disorders.

The compounds of formula I are also of interest for the treatment of epilepsy; migraines; sexual dysfunction; sleep disorders; substance abuse, including addiction to alcohol and various drugs, including cocaine and nicotine; gastrointestinal disorders, such as malfunction of gastrointestinal motility; and obesity, with its consequent comorbidities including Type II diabetes, cardiovascular disease, hypertension, hyperlipidemia, stroke, osteoarthritis, sleep apnea, gall bladder disease, gout, some cancers, some infertility, and early mortality.

The compounds of formula I can also be used to treat central nervous system deficiencies associated, for example, with trauma, stroke, and spinal cord injuries. The compounds of formula I can therefore be used to improve or inhibit further degradation of central nervous system activity during or following the malady or trauma in question. Included in these improvements are maintenance or improvement in motor and motility skills, control, coordination and strength.

In certain embodiments, the present invention therefore provides methods of treating, each of the conditions listed above in a patient, preferably in a human, the methods including administering a therapeutically effective amount of at least one compound of formula I or a pharmaceutically acceptable salt thereof to a patient suffering from such a condition.

5. Pharmaceutically Acceptable Compositions

In other embodiments, the invention relates to compositions comprising at least one compound of formula I, or a pharmaceutically acceptable salt thereof, and one or more pharmaceutically acceptable carriers, excipients, or diluents. Such compositions include pharmaceutical compositions for treating or controlling disease states or conditions of the central nervous system. In certain embodiments, the compositions comprise mixtures of one or more compounds of formula I.

In certain embodiments, the invention relates to compositions comprising at least one compound of formula I, or a pharmaceutically acceptable salt thereof, and one or more pharmaceutically acceptable carriers, excipients, or diluents. Such compositions are prepared in accordance with acceptable pharmaceutical procedures, such as, for example, those described in *Remingtons Pharmaceutical Sciences,* 17th edition, ed. Alfonoso R. Gennaro, Mack Publishing Company, Easton, Pa. (1985), which is incorporated herein by reference in its entirety. Pharmaceutically acceptable carriers are those carriers that are compatible with the other ingredients in the formulation and are biologically acceptable.

The compounds of formula I can be administered orally or parenterally, neat, or in combination with conventional pharmaceutical carriers. Applicable solid carriers can include one or more substances that can also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers can be used in preparing solutions, suspensions, emulsions, syrups and elixirs. The active ingredient can be dissolved or suspended in a pharmaceutically acceptable liquid carrier such as water, an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form.

The compounds of formula I can be administered rectally or vaginally in the form of a conventional suppository. For administration by intranasal or intrabronchial inhalation or insufflation, the compounds of formula I can be formulated into an aqueous or partially aqueous solution, which can then be utilized in the form of an aerosol. The compounds of Formula I can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The amount of compound of formula I provided to a patient will vary depending upon what is being administered, the purpose of the administration, such as prophylaxis or therapy, the state of the patient, the manner of administration, and the like. In therapeutic applications, compounds of formula I are provided to a patient suffering from a condition in an amount sufficient to treat or at least partially treat the symptoms of the condition and its complications. An amount adequate to accomplish this is a "therapeutically effective amount" as described previously herein. The dosage to be used in the treatment of a specific case must be subjectively determined by the attending physician. The variables involved include the specific condition and the size, age, and response pattern of the patient. The treatment of substance abuse follows the same method of subjective drug administration under the guidance of the attending physician. Generally, a starting dose is about 5 mg per day with gradual increase in the daily dose to about 150 mg per day, to provide the desired dosage level in the patient.

In certain embodiments, the present invention is directed to prodrugs of compounds of formula I. The term "prodrug," as used herein, means a compound that is convertible in vivo by metabolic means (e.g. by hydrolysis) to a compound of formula I. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991), Bundgaard, et al., Journal of Drug Delivery Reviews, 8:1-38(1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is hereby incorporated by reference in its entirety.

EXAMPLES

As depicted in the Examples below, in certain exemplary embodiments, compounds are prepared according to the following general procedures. It will be appreciated that although the general methods depict the synthesis of certain compounds of the present invention, the following general methods, in addition to the Schemes set forth above and other methods known to one of ordinary skill in the art, can be applied to all compounds and subclasses and species of each of these compounds, as described herein.

The following examples illustrate the preparation of representative compounds of the present invention. Each intermediate as described herein was prepared according to the methods used to prepare the same, as described in detail in U.S. patent application Ser. No. 10/970,714, filed Oct. 21, 2004, the entirety of which is hereby incorporated herein by reference.

Example 1

(R)-N-[7-(2,6-Dichloro-phenyl)-5-fluoro-2,3-dihydro-benzofuran-2-ylmethyl]-acetamide (R)-[7-(2,6-Dichloro-phenyl)-5-fluoro-2,3-dihydro-benzofuran-2-yl]-methylamine hydrochloride (0.050 g, 0.14 mmol) was suspended in 5.0 mL of methylene chloride and diisopropylethylamine (0.072 g, 0.56 mmol) and acetic anhydride (0.029 g, 0.28 mmol) added. The mixture was stirred at room temperature for 30 min, diluted to 100 mL with methylene chloride, washed with 50 mL portions of 2 N HCl (aqueous), saturated aqueous sodium bicarbonate and saturated brine. The solution was dried over sodium sulfate, filtered and concentrated in vacuum to give 0.043 g of the title compound as a white crystalline solid. $^1$H-NMR (CDCl$_3$): multiplet 7.4 δ (1H); multiplet 7.33 δ (2H); doublet 6.95 δ (1H); doublet 6.72 δ (1H); broad singlet 5.8 δ (1H); multiplet 4.9 δ (1H); doublet of doublets 3.6 δ (1H); doublet of doublets 3.47 δ (1H); doublet of doublets 3.38 δ (1H); doublet of doublets 3.0 δ (1H); singlet 1.9 δ (3H).

Example 2

N-[7-(2,6-Dichloro-phenyl)-2,3-dihydro-benzofuran-2-ylmethyl]-acetamide

[7-(2,6-Dichloro-phenyl)-2,3-dihydro-benzofuran-2-yl]-methylamine hydrochloride (0.050 g, 0.17 mmol) was suspended in 5.0 mL of methylene chloride and diisopropylethylamine (0.072 g, 0.56 mmol) and acetic anhydride (0.029 g, 0.28 mmol) added. The mixture was stirred at room temperature for 30 min, diluted to 100 mL with methylene chloride, washed with 50 mL portions of 2 N HCl (aqueous), saturated aqueous sodium bicarbonate and saturated brine. The solution was dried over sodium sulfate, filtered and concentrated in vacuum to give 0.038 g of the title compound as a white crystalline solid.

Example 3

N-[7-(2-Chloro-phenyl)-2,3-dihydro-benzofuran-2-ylmethyl]-acetamide

[7-(2-Chloro-phenyl)-2,3-dihydro-benzofuran-2-yl]-methylamine hydrochloride (0.050 g, 0.17 mmol) was suspended in 5.0 mL of methylene chloride and diisopropylethylamine (0.072 g, 0.56 mmol) and acetic anhydride (0.029 g, 0.28 mmol) added. The mixture was stirred at room temperature for 30 min, diluted to 100 mL with methylene chloride, washed with 50 mL portions of 2 N HCl (aqueous), saturated aqueous sodium bicarbonate and saturated brine. The solution was dried over sodium sulfate, filtered and concentrated in vacuum to give 0.047 g of the title compound as an oil which slowly hardened to a white solid in vacuum. $^1$H-NMR (CDCl$_3$): doublet of doublets 7.48 δ (1H); multiplet 7.33 δ (2H); doublet 7.2 δ (1H); doublet 7.06 δ (1H); triplet 6.93 δ (1H); broad singlet 5.95 δ (1H); multiplet 4.9 δ (1H); doublet of doublets 3.7 δ (1H); doublet of doublets 3.45 δ (1H); doublet of doublets 3.35 δ (1H), doublet of doublets 3.0 δ (1H), singlet 1.95 δ (3H).

Examples 4-16

The following compounds are prepared from the appropriate amine hydrochlorides in a manner substantially similar to the procedures described in Examples 1-3 above:

N-[7-(2-Trifluoromethyl-phenyl)-2,3-dihydro-benzofuran-2-ylmethyl]-acetamide;
N-[7-(2,4-Dichloro-phenyl)-2,3-dihydro-benzofuran-2-ylmethyl]-acetamide;
(R)-N-[7-(2,5-Dichloro-phenyl)-2,3-dihydro-benzofuran-2-ylmethyl]-acetamide;
N-[7-(2-Chloro-phenyl)-5-fluoro-2,3-dihydro-benzofuran-2-ylmethyl]-acetamide;
N-[5-Chloro-7-(2-chloro-phenyl)-2,3-dihydro-benzofuran-2-ylmethyl]-acetamide;
N-[7-(2-Chloro-phenyl)-5-methyl-2,3-dihydro-benzofuran-2-ylmethyl]-acetamide;
N-[7-(2-Chloro-phenyl)-5-ethyl-2,3-dihydro-benzofuran-2-ylmethyl]-acetamide;
(R)-N-[7-(2-Chloro-6-methyl-phenyl)-5-methyl-2,3-dihydro-benzofuran-2-ylmethyl]-acetamide;
(R)-N-(5-Fluoro-7-o-tolyl-2,3-dihydro-benzofuran-2-ylmethyl)-acetamide;
N-[7-(2,6-Difluoro-phenyl)-5-fluoro-2,3-dihydro-benzofuran-2-ylmethyl]-acetamide;
N-[7-(2,6-Dimethyl-phenyl)-5-fluoro-2,3-dihydro-benzofuran-2-ylmethyl]-acetamide;
N-[7-(2-Chloro-phenyl)-6-fluoro-2,3-dihydro-benzofuran-2-ylmethyl]-acetamide; and
N-(6-Fluoro-7-o-tolyl-2,3-dihydro-benzofuran-2-ylmethyl)-acetamide.

Biological Assays

The ability of the compounds of this invention to act as melatonin agonists and partial agonists is established using several standard pharmacological test procedures; the procedures are provided below.

Using a method substantially similar to that described by Audinot, V., et al, "New selective ligands of human cloned melatonin MT$_1$ and MT$_2$ receptors" *Nauyn-Schmiedeberg's Arch Pharmacol* 2003 367:553-561, human cloned MT1 and MT2 receptors are stably expressed in HEK-293 or CHO cells, the cells grown at confluence, harvested in phosphate buffer containing 2 mM EDTA and centrifuged at 1000 g and 4° C. for five minutes. The resulting pellet is suspended in 5 mM Tris/HCl, pH 7.4, containing 2 mM EDTA and homogenized using a Kinematica polytron. The homogenate is then centrifuged (20,000 g, 30 min, 4 deg C.) and the resulting pellet suspended in 75 mM Tris/HCl, pH 7.4, containing 2 mM EDTA and 12.5 mM MgCl$_2$. Aliquots of membrane preparations are stored in binding buffer (Tris/HCl 50 mM, pH 7.4, 5 mM MgCl$_2$) at −80 deg C. until use.

Membranes are incubated for 2 hours at 37° C. in binding buffer in a final volume of 250 uL containing 2-[$^{125}$I]-melatonin 20 pM for competition in CHO cells and 25 or 200 pM, respectively, for MT1 and MT2 cells expressed in HEK cells. The results are expressed as K$_i$; non-specific binding is defined with 10 uM melatonin. Reaction is stopped by rapid filtration through GF/B unifilters, followed by three successive washes with ice cold buffer. Data are analyzed by using the program PRISM (GraphPad Software, Inc., San Diego, Calif.). For saturation assay, the density of binding sites $B_{max}$ and the dissociation constant of the radioligand ($K_D$) values are calculated according to the method of Scatchard. For competition experiments, inhibition constants ($K_i$) are calculated according to the Cheng-Prussof equation: $K_i = IC_{50}/[1+(L/K_D)]$, where $IC_{50}$ is the Inhibitory Concentration 50% and L is the concentration of radioligand.

The entire disclosure of each patent, patent application, and publication cited or described in this document is hereby incorporated by reference.

While we have presented a number of embodiments of this invention, it is apparent that our basic construction can be altered to provide other embodiments which utilize the compounds and methods of this invention. Therefore, it will be appreciated that the scope of this invention is to be defined by the appended claims rather than by the specific embodiments which have been represented by way of example.

What is claimed is:

1. A compound of formula I:

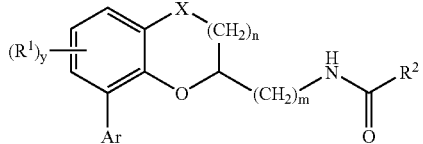

I or pharmaceutically acceptable salts thereof, wherein:
m is 1 or 2;
n is 0;
y is 0, 1, 2, or 3;
each $R^1$ is independently —CN, halogen, —R, or —OR;
each R is independently hydrogen, $C_{1-4}$ aliphatic, or fluoro-substituted $C_{1-4}$ aliphatic;
Ar is thienyl, furyl, pyridyl, or phenyl wherein Ar is optionally substituted with one or more $R^x$ groups;
each $R^x$ is independently halogen, phenyl, —CN, —R, or —OR;
$R^2$ is hydrogen or $C_{1-4}$ aliphatic; and
X is —CH$_2$—.

2. The compound according to claim 1, wherein said compound is of formula Ib:

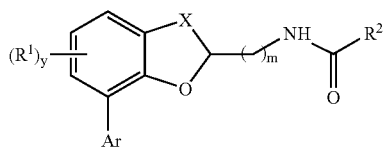

Ib or a pharmaceutically acceptable salt thereof.

3. The compound according to claim 2, wherein each $R^1$ is independently —R, halogen, —OR, or trifluoromethyl.

4. The compound according to claim 3, wherein said compound is of formula IIc or IId:

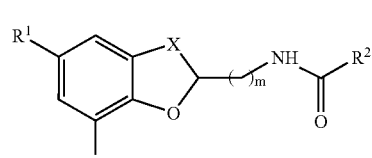

IIc

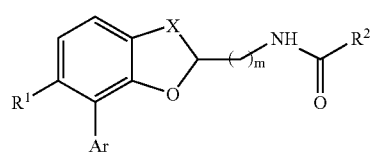

IId or a pharmaceutically acceptable salt thereof.

5. The compound according to claim 4, wherein Ar is pyridyl, thienyl, or furanyl.

6. The compound according to claim 2, wherein said compound is of formula IIIb, IVb, or IVd:

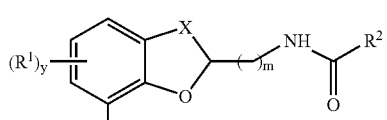

IIIb

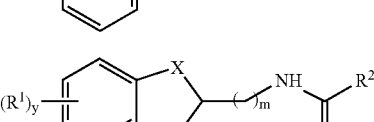

IVb

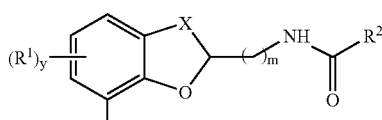

IVd or a pharmaceutically acceptable salt thereof.

7. The compound according to claim 6, wherein each $R^x$ is independently selected from —R, halogen, —OR, trifluoromethyl, —OCF$_3$.

8. The compound according to claim 6, wherein:
X is —CH$_2$—;
each $R^1$ is independently —R, —CN, halogen, or —OR;
$R^2$ is hydrogen, methyl, ethyl, propyl, cyclopropyl or cyclobutyl;
Ar is pyridyl, thienyl, furanyl, or phenyl, wherein Ar is optionally substituted with one or more $R^x$ groups; and
each $R^x$ is independently selected from —R, —CN, halogen, or —OR.

9. The compound according to claim 1, wherein said compound is selected from:

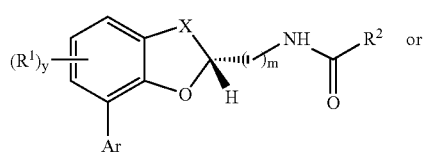
Vc
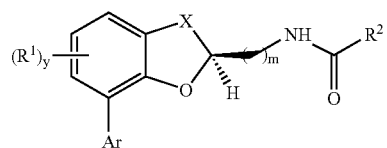
Vd
or a pharmaceutically acceptable salt thereof.
10. The compound according to claim 1, wherein said compound is selected from:
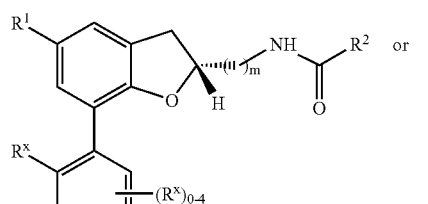
VIIa
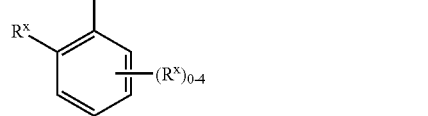
VIIb
or a pharmaceutically acceptable salt thereof.
11. The compound according to claim 1, wherein Ar is selected from:
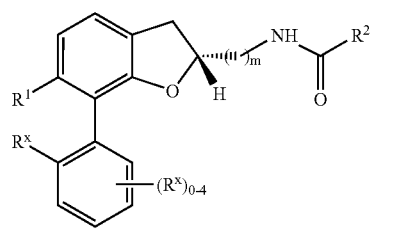
i
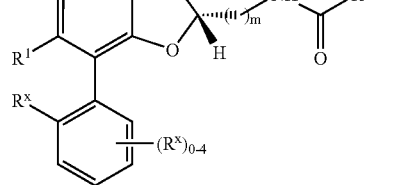
ii
-continued
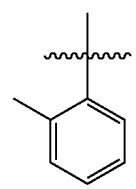
iii
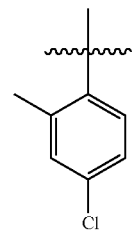
iv
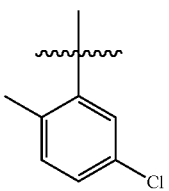
v
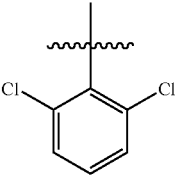
vi
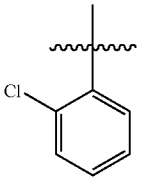
vii
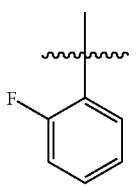
viii
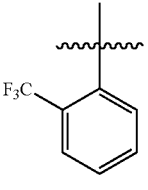
ix
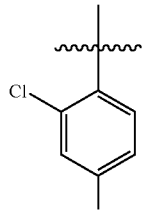
x -continued
xi
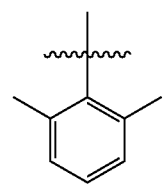
xii
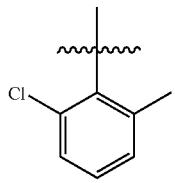
xiii
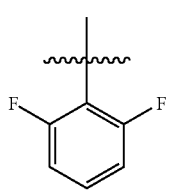
xiv
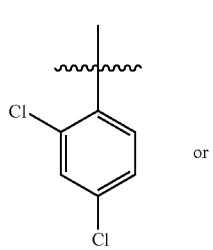 or
xv
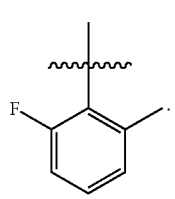.
12. The compound according to claim 1, wherein said compound is selected from:
I-1
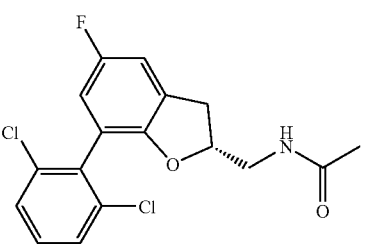
I-2
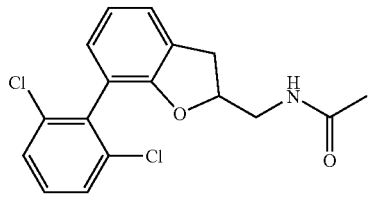
-continued
I-3
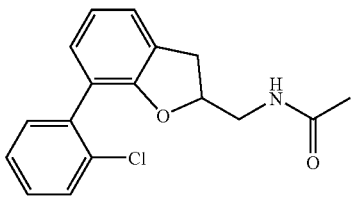
I-4
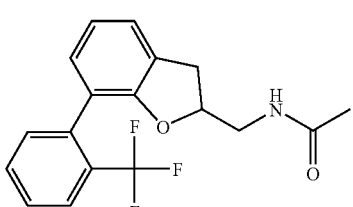
I-5
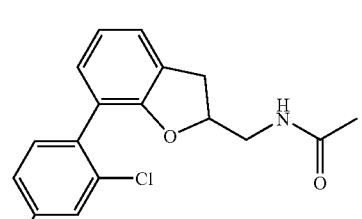
I-6
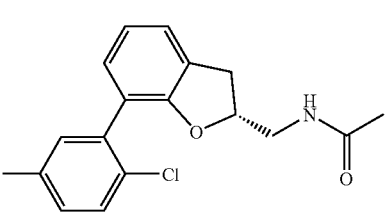
I-7
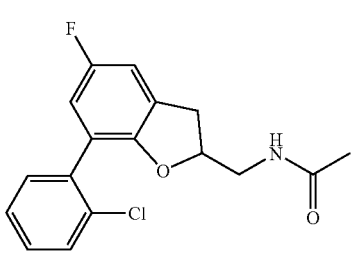
I-8
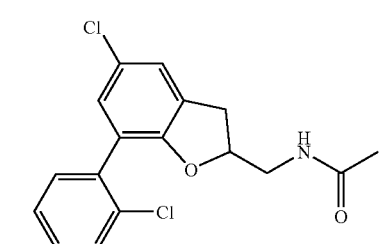
I-9
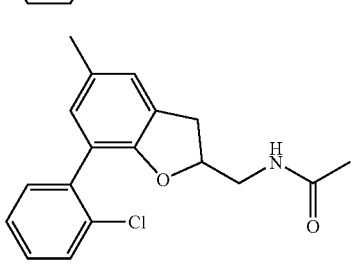

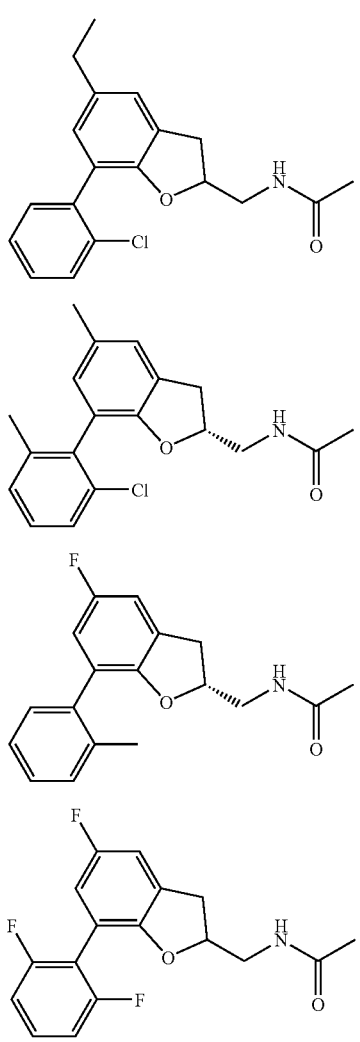
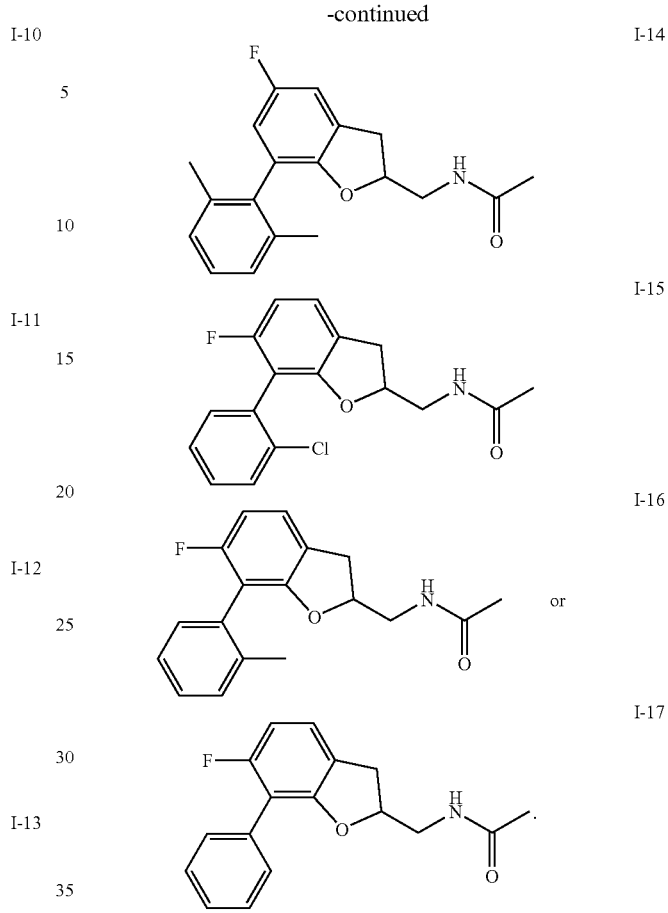
13. A composition comprising a compound according to claim 1, and one or more pharmaceutically acceptable carriers.
* * * * *